(12) United States Patent
Alameh et al.

(10) Patent No.: US 11,902,091 B2
(45) Date of Patent: Feb. 13, 2024

(54) ADAPTING A DEVICE TO A USER BASED ON USER EMOTIONAL STATE

(71) Applicant: Motorola Mobility LLC, Chicago, IL (US)

(72) Inventors: Rachid M. Alameh, Crystal Lake, IL (US); Zhengping Ji, Hinsdale, IL (US); Alvin Von Ruff, Woodstock, IL (US)

(73) Assignee: Motorola Mobility LLC, Chicago, IL (US)

( * ) Notice: Subject to any disclaimer, the term of this patent is extended or adjusted under 35 U.S.C. 154(b) by 145 days.

(21) Appl. No.: 16/861,873

(22) Filed: Apr. 29, 2020

(65) Prior Publication Data

US 2021/0344560 A1 Nov. 4, 2021

(51) Int. Cl.
*H04L 12/24* (2006.01)
*G06F 3/01* (2006.01)
*G06N 20/00* (2019.01)
*H04L 41/0816* (2022.01)
*A61B 5/16* (2006.01)
*G06N 5/04* (2023.01)
(Continued)

(52) U.S. Cl.
CPC .......... *H04L 41/0816* (2013.01); *A61B 5/165* (2013.01); *G06F 3/011* (2013.01); *G06N 5/04* (2013.01); *G06N 20/00* (2019.01); *A61B 5/024* (2013.01); *A61B 5/1172* (2013.01); *G06F 2203/011* (2013.01)

(58) Field of Classification Search
CPC .. G06F 3/011; G06F 2203/011; A61B 5/1123; A61B 5/024; A61B 5/0022; A61B 5/7475; A61B 5/4803; A61B 2562/0204; A61B 5/6898; A61B 2560/02421; A61B 5/165; A61B 2562/0219; A61B 2562/0223; A61B 5/1172; A61B 5/02055; H04L 41/161; H04L 41/0816; G06N 20/00; G06N 5/04
See application file for complete search history.

(56) References Cited

U.S. PATENT DOCUMENTS 7,725,419 B2 *  5/2010  Lee .......................... G06F 3/011
                                                      706/60
8,489,599 B2 *  7/2013  Bellotti ............... G06F 16/4393
                                                      707/736
(Continued)

OTHER PUBLICATIONS

"Affectiva—App", Retrieved at: https://www.affectiva.com/—on Feb. 24, 2020, 9 pages.
(Continued)

*Primary Examiner* — Abdullahi E Salad
(74) *Attorney, Agent, or Firm* — FIG. 1 Patents

(57) ABSTRACT

A change in the emotional state of a user of a device is detected, and in response to this change a reason for the change in user emotional state is determined. This determination is made based on both the current user emotional state and context data for the device or user. The device then adapts to the user based on the current emotional state and the reason for the change in user emotional state. This adaptation of the computing device refers to an alteration of the operation of the computing device with a goal of increasing the likelihood of the user being in a good emotional state (e.g., happy, relaxed) and reducing the likelihood of the user being in a bad emotional state (e.g., sad, angry).

20 Claims, 6 Drawing Sheets

(51) Int. Cl.
*A61B 5/1172* (2016.01)
*A61B 5/024* (2006.01)

(56) References Cited

U.S. PATENT DOCUMENTS

| | | | | |
|---|---|---|---|---|
| 8,683,348 | B1* | 3/2014 | Blank | G06F 3/038 |
| | | | | 715/709 |
| 8,701,003 | B2* | 4/2014 | Kondziela | G06F 3/011 |
| | | | | 715/744 |
| 10,200,725 | B2* | 2/2019 | Tatourian | G09G 5/391 |
| 10,514,766 | B2* | 12/2019 | Gates | G06F 3/017 |
| 2008/0160976 | A1* | 7/2008 | Virolainen | H04L 65/765 |
| | | | | 455/416 |
| 2012/0083668 | A1* | 4/2012 | Pradeep | A61B 5/6803 |
| | | | | 600/300 |
| 2013/0159228 | A1* | 6/2013 | Meijer | G06F 9/451 |
| | | | | 706/14 |
| 2013/0260348 | A1* | 10/2013 | Blow | G09B 19/00 |
| | | | | 434/236 |
| 2014/0075348 | A1* | 3/2014 | Sathish | G01C 21/3682 |
| | | | | 715/764 |
| 2014/0100835 | A1* | 4/2014 | Majumdar | G06Q 10/04 |
| | | | | 703/11 |
| 2014/0244782 | A1* | 8/2014 | Beaurepaire | H04W 4/029 |
| | | | | 709/217 |
| 2016/0063874 | A1* | 3/2016 | Czerwinski | G16H 50/20 |
| | | | | 434/236 |
| 2017/0289766 | A1* | 10/2017 | Scott | H04W 8/005 |
| 2017/0322679 | A1* | 11/2017 | Gordon | G06N 20/00 |
| 2018/0005442 | A1* | 1/2018 | Mullins | G06T 19/006 |
| 2019/0329165 | A1* | 10/2019 | Backman | B01D 33/466 |
| 2020/0004583 | A1* | 1/2020 | Kelly | G06N 7/01 |
| 2020/0206631 | A1* | 7/2020 | Sumant | G06V 40/20 |
| 2021/0217423 | A1* | 7/2021 | Rakshit | G10L 15/22 |

OTHER PUBLICATIONS

"Daylio Journal", Retrieved at: https://apps.apple.com/us/app/daylio-journal-diary-moods/id1194023242—on Feb. 24, 2020, 2 pages.

"Emotion Detection from Speech Signals", Retrieved at: https://www.youtube.com/watch?v=RbfGmX8Qrbg, Jul. 27, 2016, 1 page.

"Exist—App", Retrieved at: https://exist.io/—on Feb. 24, 2020, 11 pages.

Bond, "SenseCare: Using Affective Computing to Manage and Care for the Emotional Wellbeing of Older People", Jan. 2017, pp. 352-356.

Chernykh, "Emotion Recognition from Speech with Recurrent Neural Networks", Jul. 5, 2018, 18 pages.

Kleinberger, "Why you don't like the sound of your own voice", Retrieved at: https://www.youtube.com/watch?v=g3vSYbT1Aco&feature=youtu.be, May 24, 2018, 1 page.

Picard, "Computers that Recognize and Respond to User Emotion: Theoretical and Practical Implications", Nov. 12, 2001, 26 pages.

Pradhan, "Passive Mood Tracking with the Feel Wristband", Jun. 2, 2016, 7 pages.

\* cited by examiner

ADAPTING A DEVICE TO A USER BASED ON USER EMOTIONAL STATE

BACKGROUND

As technology has advanced, computing devices have become increasingly commonplace in our lives. People can be found using their computing devices at home, at work, while shopping, while driving, while dining out, and so forth. Situations can arise, however, in which computing devices do not operate as their users desire. For example, situations can arise in which a user desires to provide voice input to his computing device while in a noisy environment, but the computing device is unable to understand his input due to the noise. Situations can also arise in which other contextual environment factors that can be sensed by a computing device interferes with its user's desired use of the computing device, such as distractions, bad conversations, words, topics, user aggravation, rain, noise, traffic, driving, time of day, location, user wellness condition, pending schedules, user rushing, people user is engaging with through the device or around the device, and so forth. These situations can lead to user frustration and dissatisfaction with their devices.

BRIEF DESCRIPTION OF THE DRAWINGS

Embodiments of adapting a device to a user based on to user emotional state are described with reference to the following drawings. The same numbers are used throughout the drawings to reference like features and components.

DETAILED DESCRIPTION

Adapting a device to a user based on user emotional state is discussed herein. Generally, an emotional state based adaptation system receives and analyzes user data to determine an emotional state of the user of a computing device while the user is engaged with the computing device. This user engagement with the computing device refers to any user input to or interaction with the computing device. Context data is also collected while the user is engaged with the computing device. The context data can include one or both of environment data describing the environment in which the computing device (or user of the device) is present and sensory data associated with or tied to a user (or associated with or tied to a user input).

A change in the user emotional state is detected, and in response to this change a reason for the change in user emotional state is determined. This determination is made based on both the current (the changed to) user emotional state and the context data. The computing device then adapts to the user based on the current emotional state and the reason for the change in user emotional state. This adaptation of the computing device refers to an alteration of the operation of the computing device with a goal of increasing the likelihood of the user being in a good emotional state (e.g., happy, relaxed) and reducing the likelihood of the user being in a bad emotional state (e.g., sad, angry). For example, this adaptation can include prompting the user to provide a text input in response to the computing device being in a noisy environment and multiple unsuccessful user attempts to input a voice command.

The techniques discussed herein improve the operation of the computing device by adapting the computing device to account for changes in user emotional state. This adaptation of the computing device increases the likelihood of the user being in a good emotional state while using the computing device, resulting in an improved user experience with the computing device.

Figure 1:
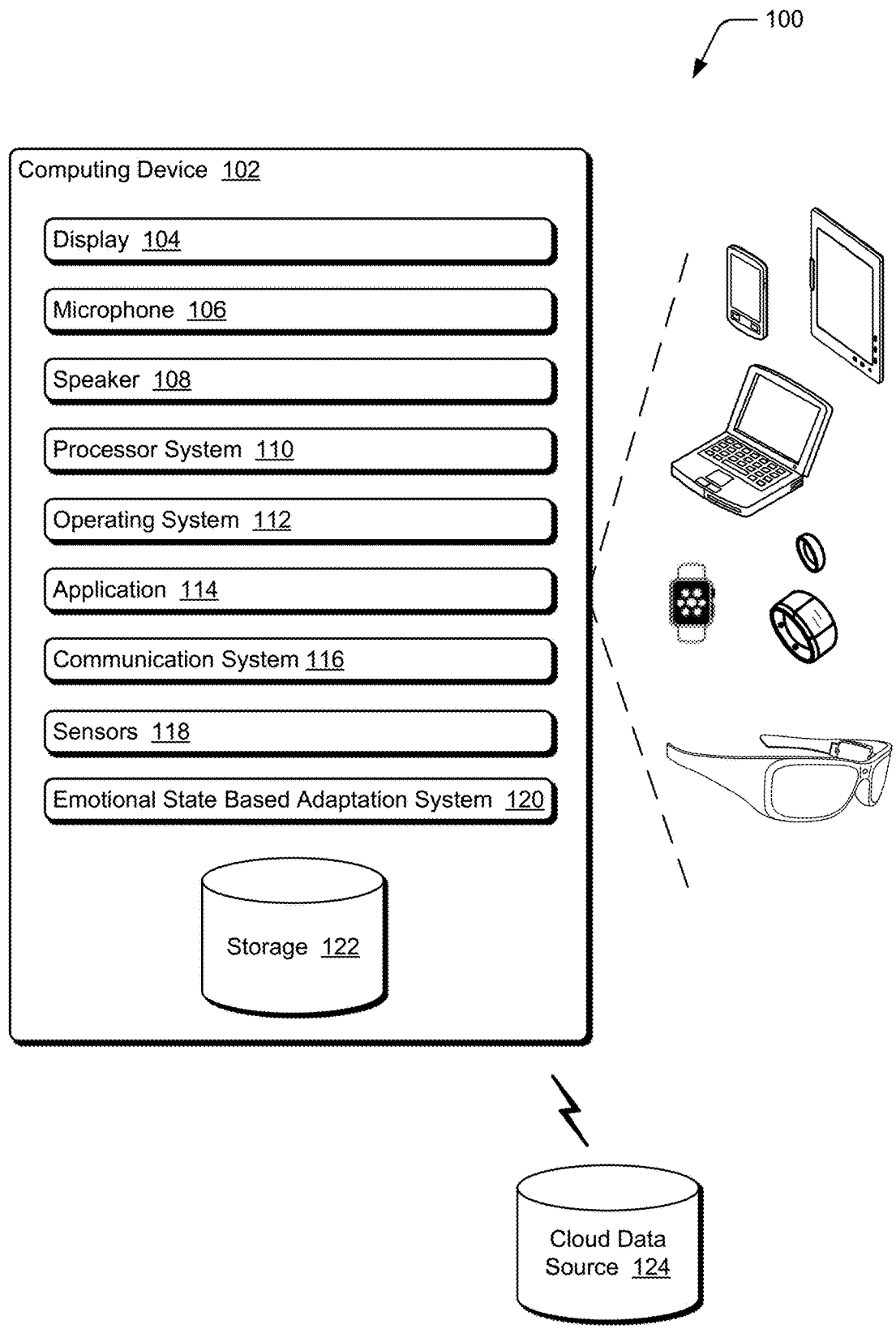
FIG. 1 illustrates an example system implementing the techniques discussed herein.

FIG. 1 illustrates an example system 100 implementing the techniques discussed herein. The system 100 includes a computing device 102 that can be, or include, many different types of computing or electronic devices. For example, the computing device 102 can be a smartphone or other wireless phone, a notebook computer (e.g., netbook or ultrabook), a laptop computer, a camera (e.g., compact or single-lens reflex), a wearable device (e.g., a smartwatch, a ring or other jewelry, augmented reality headsets or glasses, virtual reality headsets or glasses), a tablet or phablet computer, a personal media player, a personal navigating device (e.g., global positioning system), an entertainment device (e.g., a gaming console, a portable gaming device, a streaming media player, a digital video recorder, a music or other audio playback device), a video camera, an Internet of Things (IoT) device, a fitness tracker, a smart TV, an automotive computer, and so forth.

The computing device 102 includes a display 104, a microphone 106, and a speaker 108. The display 104 can be configured as any suitable type of display, such as an organic light-emitting diode (OLED) display, active matrix OLED display, liquid crystal display (LCD), in-plane shifting LCD, projector, and so forth. The microphone 106 can be configured as any suitable type of microphone incorporating a transducer that converts sound into an electrical signal, such as a dynamic microphone, a condenser microphone, a piezoelectric microphone, and so forth. The speaker 108 can be configured as any suitable type of speaker incorporating a transducer that converts an electrical signal into sound, such as a dynamic loudspeaker using a diaphragm, a piezoelectric speaker, non-diaphragm based speakers, and so forth.

Although illustrated as part of the computing device 102, it should be noted that one or more of the display 104, the microphone 106, and the speaker 108 can be implemented separately from the computing device 102. In such situations, the computing device 102 can communicate with the display 104, the microphone 106, and/or the speaker 108 via any of a variety of wired (e.g., Universal Serial Bus (USB), IEEE 1394, High-Definition Multimedia Interface (HDMI)) or wireless (e.g., Wi-Fi, Bluetooth, infrared (IR)) connections. For example, the display 104 may be separate from the computing device 102 and the computing device 102 (e.g., a streaming media player) communicates with the display 104 via an HDMI cable. By way of another example, the microphone 106 may be separate from the computing device 102 (e.g., the computing device 102 may be a television and the microphone 106 may be implemented in a remote control device) and voice inputs received by the microphone 106 are communicated to the computing device 102 via an IR or radio frequency wireless connection.

The computing device 102 also includes a processor system 110 that includes one or more processors, each of which can include one or more cores. The processor system 110 is coupled with, and may implement functionalities of, any other components or modules of the computing device 102 that are described herein. In one or more embodiments, the processor system 110 includes a single processor having a single core. Alternatively, the processor system 110 includes a single processor having multiple cores and/or multiple processors (each having one or more cores).

The computing device 102 also includes an operating system 112. The operating system 112 manages hardware, software, and firmware resources in the computing device 102. The operating system 112 manages one or more applications 114 running on the computing device 102, and operates as an interface between applications 114 and hardware components of the computing device 102.

The computing device 102 also includes a communication system 116. The communication system manages communication with various other devices, including establishing voice calls with other devices, messaging with other devices, and so forth. This communication can take various forms, such as voice calls (e.g., over a cellular system, public switched telephone network (PSTN), network (e.g., using voice over Internet Protocol (VoIP), etc.), short messaging service (SMS) messages, multimedia messaging service (MMS) messages, and so forth.

The computing device 102 also includes one or more sensors 118. A variety of different types of sensors 118 can be included in the computing device 102, such as an image capture device (e.g., a camera), a biometric data sensor (e.g., a heart rate sensor, a fingerprint sensor), a motion sensor (e.g., an accelerometer, a gyroscope, a magnetic field sensor), a thermal sensor, a proximity sensor, an active IR sensor, a passive IR sensor, a microphone, a motion sensor, an elevation sensor, an ultrasound sensor, and so forth. These sensors 118 detect or sense various environment data for the computing device 102 as discussed in more detail below. Although illustrated separately, it should be noted that the microphone 106 can also be considered a sensor 118.

The computing device 102 also includes an emotional state based adaptation system 120. The emotional state based adaptation system 120 determines when the emotional state of a user that is engaged with the computing device 102 changes from one emotional state to another (deviates from the norm for the user based on prior history) and further determines the reason for the change in emotional state. The emotional state based adaptation system 120 also alters the operation of the computing device based on the reason for the change in emotional state as discussed in more detail below.

The emotional state based adaptation system 120 can be implemented in a variety of different manners. For example, the emotional state based adaptation system 120 can be implemented as multiple instructions stored on computer-readable storage media and that can be executed by the processor system 110. Additionally or alternatively, the emotional state based adaptation system 120 can be implemented at least in part in hardware (e.g., as an application-specific integrated circuit (ASIC), a field-programmable gate array (FPGA), and so forth).

The computing device 102 also includes a storage device 122. The storage device 122 can be implemented using any of a variety of storage technologies, such as magnetic disk, optical disc, Flash or other solid state memory, and so forth.

The storage device 122 can store various program instructions and data for the operating system 112, application 114, and/or emotional state based adaptation system 120.

The system 100 also includes a cloud data source 124. The cloud data source 124 maintains and provides to the computing device 102 various environment data for the computing device 102 as discussed in more detail below. The cloud data source 124 can be implemented as any of a variety of different types of computing devices (e.g., any of the types discussed above with reference to computing device 102), a database or other data store, and so forth. The cloud data source 124 can provide environment data to the computing device 102 via any of a variety of different networks, such as the Internet, a local area network (LAN), a public telephone network, an intranet, other public or proprietary networks, combinations thereof, and so forth.

Figure 2:
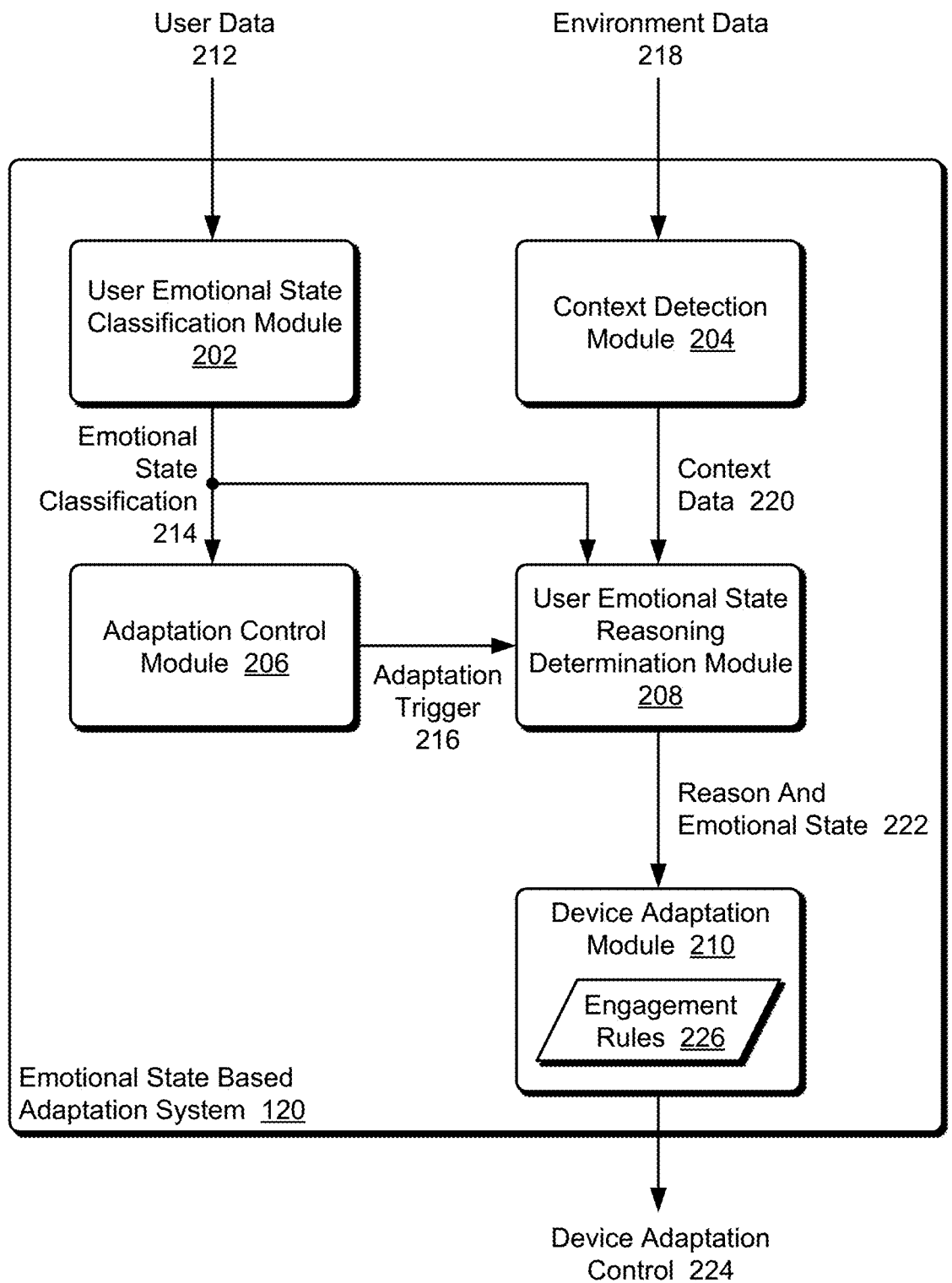
FIG. 2 illustrates an example emotional state based adaptation system in accordance with one or more embodiments.

FIG. 2 illustrates an example emotional state based adaptation system 120 in accordance with one or more embodiments. The emotional state based adaptation system 120 includes a user emotional state classification module 202, a context detection module 204, an adaptation control module 206, a user emotional state reasoning determination module 208, and a device adaptation module 210. The emotional state based adaptation system 120 alters the operation of a device (e.g., the computing device 102 of FIG. 1) based on a reason for a change in emotional state of the user of the device.

Generally, the user emotional state classification module 202 receives and analyzes user data 212 to determine an emotional state of the user of the device. The user emotional state classification module 202 provides an indication of the emotional state of the user to the adaptation control module 206 as emotional state classification 214. The adaptation control module 206 determines when there has been a change in the emotional state of the user and provides an adaptation trigger 216 to the user emotional state reasoning determination module 208 indicating that the change in emotional state.

The context detection module 204 monitors the context of the device or user based on received environment data 218 and provides context data 220 to the user emotional state reasoning determination module 208 describing the context of the device or user, the contextual situation, or the surrounding environment. The user emotional state reasoning determination module 208 determines, based on the context data 220 and the emotional state of the user, a reason for the change in emotional state of the user. The user emotional state reasoning determination module 208 provides the determined reason and user emotional state 222 to the device adaptation module 210. The device adaptation module 210 determines an adaptation to alter the operation of the device based on the reason and emotional state 222, and outputs a device adaptation control 224 to alter the operation of the device based on the determined adaptation.

More specifically, the user emotional state classification module 202 implements functionality to determine an emotional state of a user of the device. The user emotional state classification module 202 receives user data 212 that describes the manner in which the user is interacting with the device. The user data 212 can be sensed by sensors of the device (e.g., any one or more of the sensors 118 of FIG. 1). The user data 212 can also be sensed by sensors of one or more additional devices that transmit the user data 212 to the device. For example, the emotional state based adaptation system 120 can be implemented by a mobile device (e.g., a smartphone) and receive user data 212 from sensors of the mobile device as well as one or more wearable devices that are being worn by the user.

The user data 212 can include any data that may indicate the emotional state of the user. In one or more embodiments, the user data 212 includes data describing the face of the user, such as the color of the user's face (e.g., whether the user's face is red), whether the user is smiling, whether the user is frowning, whether the user is scowling, how open the user's eyes are, and so forth. Additionally or alternatively, the user data 212 can include data describing the voice of the user, such as how loud the user is, what words the user is speaking, whether the user is using profanity or angry words, whether there is a shift in frequency or acoustical response of the user's speech, and so forth.

Additionally or alternatively, the user data 212 can include data describing motions or activity of the user, such as whether the user is moving, how quickly the user is moving, which appendages the user is moving, whether the user is standing, sitting, or laying down, and so forth. Additionally or alternatively, the user data 212 can include data describing biometric information of the user, such as skin temperature of the user, heart rate of the user, whether the user is perspiring, blood pressure of the user, loudness of the user, aggravation of the user, agitation of the user (e.g., sensed via a microphone), and so forth.

The user emotional state classification module 202 classifies the emotional state of the user based on the user data 212. Any of a variety of different public or proprietary techniques can be used to classify the emotional state of the user. In one or more embodiments, the user emotional state classification module 202 is implemented using any of a variety of different public or proprietary machine learning systems. Machine learning systems refer to a computer representation that can be tuned (e.g., trained) based on inputs to approximate unknown functions. In particular, machine learning systems can include a system that utilizes algorithms to learn from, and make predictions on, known data by analyzing the known data to learn to generate outputs that reflect patterns and attributes of the known data. For instance, a machine learning system can include decision trees, support vector machines, linear regression, logistic regression, Bayesian networks, random forest learning, dimensionality reduction algorithms, boosting algorithms, artificial neural networks, deep learning, and so forth.

The user emotional state classification module 202 classifies the current emotional state of the user as one of multiple emotional state categories or classifications. For example, these multiple emotional state categories or classifications can be any two or more of angry, agitated, happy, alert, tired, sluggish, loud, relaxed, tired, sad, and so forth.

The machine learning system is trained to classify the current emotional state of the user as one of the multiple emotional state categories or classifications and notes any changes from the norm for the user. In one or more embodiments, the machine learning system is initially trained (e.g., using supervised or unsupervised learning), such as by a developer or distributor of the emotional state based adaptation system 120. The machine learning system is then further trained (e.g., using supervised or unsupervised learning) during use of the emotional state based adaptation system 120 by a user so that the machine learning system becomes customized to that user. Thus, the machine learning system learns what particular user data 212 indicates what emotional state for the particular user (e.g., a particular behavior, such as use of particular words, may indicate an angry emotional state for one user but a normal or happy emotional state for another user). The machine learning system can be trained in any of a variety of different manners depending on the type of machine learning system, such as by updating connection weights or weights of filters in the machine learning system to minimize a loss between the emotional state classification generated from user data and a known emotional state for the user data.

In one or more embodiments, the user data 212 is also communicated to an additional service or device (e.g., via the Internet). This allows the machine learning system of the user emotional state classification module to be pre-trained by the additional service or device based on user data from multiple different users. This pre-trained machine learning system can then be provided to emotional state based adaptation systems of other users and used as an initial machine learning system that is subsequently customized for each of those other users.

The context detection module 204 implements functionality to monitor the context of the device based on received environment data 218. The context of the device refers to the environment that the device is in or information associated with a user (or associated with a user input) that can be sensed. The context detection module 204 provides this environment data 218 to the user emotional state reasoning determination module 208 as context data 220.

The context of the device can include environment data 218 describing the environment in which the device (or user of the device) is present. The environment data 218 can include, for example, data describing the background of the device (e.g., how bright or light the environment is, a temperature of the environment, precipitation or humidity of the environment, noise level of the environment), data describing whether people other than the user are in the presence of the device (e.g., whether the user is alone, how many other people are with the user, which other people are around or engaging with the user), the motion of the device (e.g., the speed of the device, whether the device is moving), a location of the device (e.g., whether the device is at the user's home or office, a type of business or facility that the device is at), physical activity of the device (e.g., whether the device is in a vehicle, whether the device is with a user that is walking, whether the device is with a user that is cycling), a current time or date, acoustic detections (e.g., sounds made by the user, background sounds, noises), scene detections (e.g., whether the user is in a crowd, whether the user is at the beach), conversations (e.g., words the user is saying, words another person talking to the user is saying), loudness, speech, and so forth.

The context of the device can also include sensory data associated with or tied to a user (or associated with or tied to a user input). The sensory data can include, for example, actions the user is taking (e.g., whether the user is driving, whether the user is walking, whether the user is running), device functionality (e.g., an operation on the device being performed or requested by the user, resources or capabilities of the device the user is providing input to), active applications on the device (e.g., which applications are currently running on the device, which applications are currently providing output or feedback on the device), keywords spoken by the user, communication from the user (e.g., whether the user is providing voice input, whether the user is providing touchscreen input), how the user is holding the device (e.g., whether the user is holding the device, whether the user is holding the device with a tight grip, whether the user is holding the device with his left hand, whether the user is holding the device with his right hand), and so forth.

The environment data 218 can be sensed by sensors of the device (e.g., any one or more of the sensors 118 of FIG. 1). Additionally or alternatively, the environment data 218 can also be sensed by sensors of one or more additional devices that transmit the environment data 218 to the device. For example, the emotional state based adaptation system 120 can be implemented by a mobile device (e.g., a smartphone) and receive environment data 218 sensed by sensors of the mobile device as well as environment data 218 sensed by sensors of one or more wearable devices that are being worn by the user. Additionally or alternatively, the environment data 218 can be received from a remote service or device, such as via "the cloud" (e.g., from cloud data source 124 of FIG. 1). For example, environment data 218 could be data stored on a remote service (e.g., user engagement history, user calendar), data otherwise available from a remote service (e.g., user location data, user travel speed data, traffic data, weather data, allergen data), and so forth.

In one or more embodiments, the user data 212 and environment data 218 is collected in response to user engagement with the device. Additionally or alternatively, the user data 212 is collected in response to user engagement with the device and the environment data is collected in response to the adaptation control module 206 determining there has been a change in the emotional state of the user.

User engagement with the device refers to any user input to or interaction with the device. The user can engage with the device in various manners, such as by touch, voice input, image input, and so forth. The collection can be performed in various manners, such as by transmitting activation signals (e.g., from the emotional state based adaptation system or some other system) to the various sensors to collect data in response to user engagement with the device. The collection of the user data 212 and the environment data 218 subsequently stops in response to user disengagement from the device (e.g., the user ceases interacting with the device for a threshold amount of time, such as 20 seconds). The collection can be stopped in various manners, such as by transmitting deactivation signals (e.g., from the emotional state based adaptation system or some other system) to the various sensors to cease collecting data in response to user disengagement with the device.

Collecting the user data 212 and environment data 218 in response to user engagement with the device allows the emotional state based adaptation system 120 to adapt the device to the user emotional state when the user is engaged with the device but need not be concerned with doing so when the user is not engaged with the device. This reduces energy usage by the device as well as usage of other resources by the device because the emotional state based adaptation system 120 need not expend energy or other resources during times when the user is not engaged with the device. This improves privacy of the device too because the emotional state based adaptation system 120 need not constantly monitor the user data 212 and the environment data 218. Thus, when the user is not engaged with the device the user can know that the emotional state based adaptation system 120 is not listening to or otherwise monitoring the user.

The adaptation control module 206 implements functionality to determine when there has been a change in the emotional state of the user. The user emotional state classification module 202 generates the emotional state classification 214 at regular or irregular intervals (e.g., approximately every second) while the user is engaged with the device. The adaptation control module 206 receives the emotional state classification 214 and determines when the classification has changed. In response to determining that the classification has changed, the adaptation control module 206 provides an adaptation trigger 216 to the user emotional state reasoning determination module 208 indicating that the user emotional state has changed from a previous user emotional state to a current user emotional state. This adaptation trigger 216 notifies the user emotional state reasoning determination module 208 to determine the reason for the change in user emotional state and suggest a course of action (e.g., make the call later, wait a bit, avoid performing a requested operation, make the user aware of the detected emotions, maintain a change until the context of the device changes, pinpoint the likely cause for the new emotion, suggest an alternative operation or input).

The user emotional state classification module 202 also provides the emotional state classification 214 to the user emotional state reasoning determination module 208 approximately concurrently with providing the emotional state classification 214 to the adaptation control module 206. The user emotional state reasoning determination module 208 can assume that, in response to the adaptation trigger 216, the most recently received emotional state classification is the current emotional state classification. Additionally or alternatively, the adaptation control module 206 can provide an indication of the current emotional state classification to the user emotional state reasoning determination module 208.

The user emotional state reasoning determination module 208 implements functionality to determine, based on the context data 220 and the emotional state classification 214, a reason for the change in emotional state of the user. The user emotional state reasoning determination module 208 makes this determination in response to the adaptation trigger 216 indicating that the user emotional state has changed. For example, if the previous user emotional state was happy and the current user emotional state is angry, the user emotional state reasoning determination module 208 determines a reason why the user became angry.

In one or more embodiments, the user emotional state reasoning determination module 208 is implemented using any of a variety of different public or proprietary machine learning systems. For example, the user emotional state reasoning determination module 208 can be implemented as a decision tree, support vector machine, linear regression system, logistic regression system, Bayesian network, random forest learning system, dimensionality reduction algorithm, boosting algorithm, artificial neural network, deep learning system, and so forth. Additionally or alternatively, the user emotional state reasoning determination module 208 can be implemented using various other algorithms, rules, criteria, and so forth.

The user emotional state reasoning determination module 208 determines the reason for the change in user emotional state and outputs the determined reason and current emotional state 222. The reason for the change is also referred to as the main cause for the current emotional state. The reason for the change can be any one or combination of the environment data 218. For example, the reason for the change in user emotional state may be determined to be the noise level of the environment is too high, the brightness of the environment is too low, the user is not holding the device and the number of people around or engaging with the user is too high, the performance of the device is too low, a particular word or phrase was spoken, the person the user is engaging with, distraction of nearby conversations, and so forth.

Figure 3:
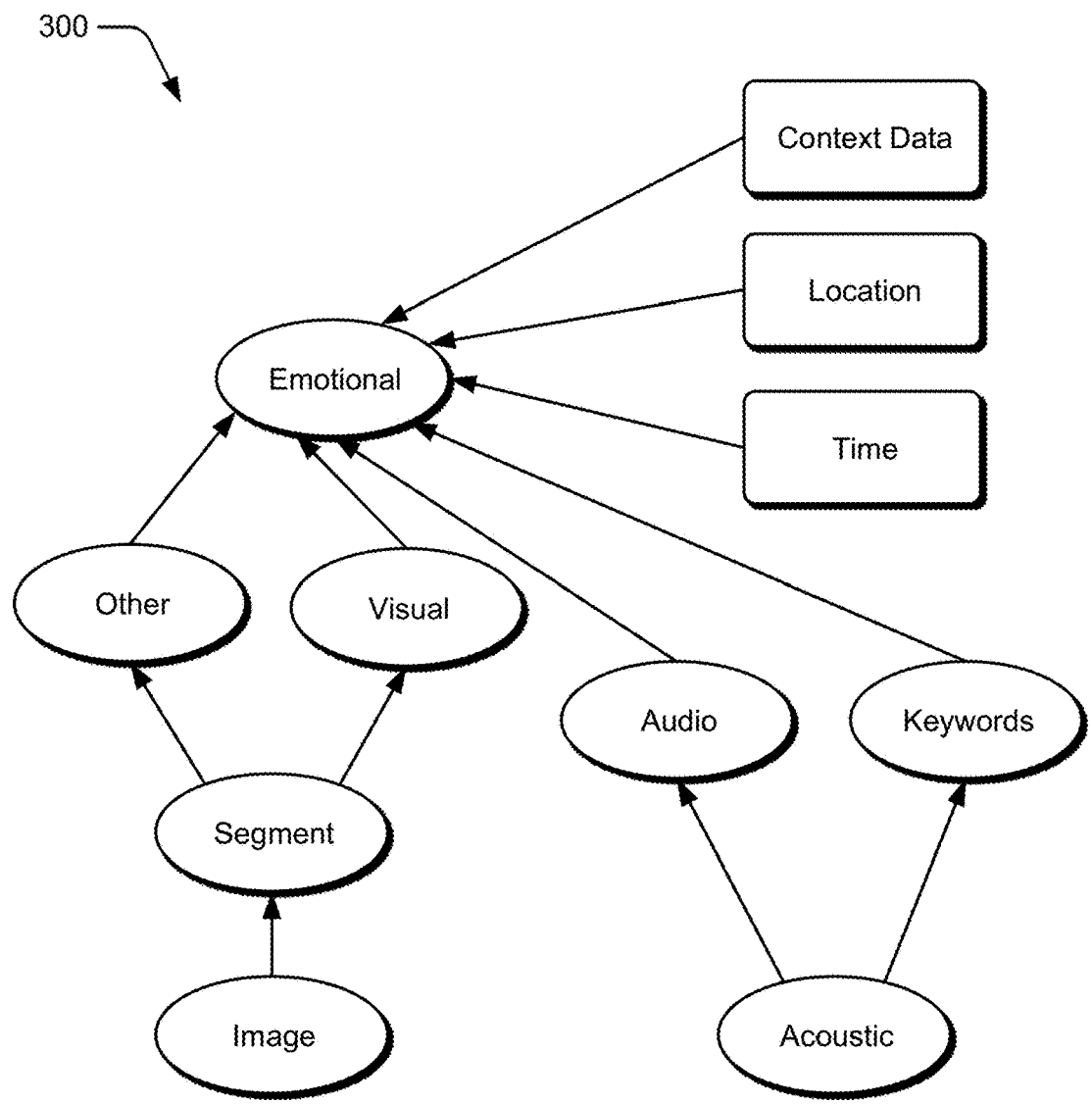
FIG. 3 illustrates an example of a machine learning system that can be implemented by the user emotional state reasoning determination module.

FIG. 3 illustrates an example of a machine learning system that can be implemented by the user emotional state reasoning determination module 208. A Bayesian network 300 is illustrated to map facial motion, audio features, and additional context (location and time) to emotional state. The network 300 is trained to learn the connection weights (the connection probabilities from one node to another) within the graph that will establish an overall likelihood from the facial motion, audio features, and additional context (location and time) observations to an emotional state.

Returning to FIG. 2, the machine learning system of the user emotional state reasoning determination module 208 is trained to determine the reason for the change in user emotional state. This training is performed during use of the emotional state based adaptation system 120 by the user so that the machine learning system becomes customized to that user. The result is a machine learning system that learns what makes a particular user be in (or change to) a particular emotional state and deviates from the norm for that particular user. For example, the machine learning system learns what makes the particular user angry.

The training of the machine learning system can be performed at various regular or irregular intervals, such as daily. This training can be unsupervised or supervised. In one or more embodiments, the user is prompted to provide input describing what puts him in a particular emotional state (e.g., aggravating things to avoid). For example, the user can be provided with a checklist of various conditions (e.g., any of the various environment data 218) and he selects those that he knows put him in a particular emotional state. Additionally or alternatively, the user is prompted to provide input describing what put him in a particular emotional state at a particular earlier time during the day (optionally not at the time the emotional state was detected so as to avoid asking an angry user why he's angry). The machine learning system can be trained in any of a variety of different manners depending on the type of machine learning system, such as by updating connection weights or weights of filters in the machine learning system to minimize a loss between A) the reason generated from an emotional state classification and context data and B) a known reason generated for the emotional state classification and context data.

Additionally or alternatively, in training the machine learning system a training component of the user emotional state reasoning determination module 208 monitors particular environment data 218 (e.g., voice analysis is performed on audio input to determine whether another party asks the user particular questions, such as "are you okay?"). The training component can determine that the current environment data 218 caused the user to be in a particular emotional state (e.g., angry or agitated) in response to one of the particular questions being asked by another party.

Additionally or alternatively, the machine learning system implemented by the user emotional state reasoning determination module 208 is initially trained (e.g., using supervised or unsupervised learning), such as by a developer or distributor of the user emotional state reasoning determination module 208. The machine learning system is then further trained during use of the emotional state based adaptation system 120 by a user so that the machine learning system becomes customized to that user.

In one or more embodiments, the context data 220 as well as the reason and emotional state 222 are also communicated to an additional service or device (e.g., via the Internet). This allows the machine learning system of the user emotional state reasoning determination module to be pre-trained by the additional service or device based on context data as well as reason and emotional state from multiple different users. This pre-trained machine learning system can then be provided to emotional state based adaptation systems of other users and used as an initial machine learning system that is subsequently customized for each of those other users.

The device adaptation module 210 implements functionality to determine to adapt the device to the user based on the received reason and emotional state 222. The device adaptation module 210 outputs a device adaptation control 224 to alter the operation of the device to adapt the device to the user. In one or more embodiments the goal of the device adaptation module 210 is to increase the likelihood of the user being in a good emotional state (e.g., happy, relaxed) and reduce the likelihood of the user being in a bad emotional state (e.g., sad, angry). If the user has changed from a good emotional state to a bad emotional state, then the device adaptation module 210 determines an adaptation to be made to return the user to a good emotional state. If the user has changed from a bad emotional state to a good emotional state, then the device adaptation module 210 need make no adaptation.

The device adaptation module 210 selects from multiple different device adaptation options that are deemed emotionally friendly and likely to change the user emotional state to a good emotional state. In one or more embodiments, the device adaptation module 210 accesses a set of engagement rules 226 that indicate one or more device adaptations to perform given the received reason and emotional state 222. Each engagement rule in the set of engagement rules 226 indicates a device adaptation to make in response to a particular reason and emotional state 222. These engagement rules can be obtained in various manners, such as being pre-configured in the device adaptation module 210, obtained from a remote device or service, and so forth.

The engagement rules 226 can indicate any of a variety of different device adaptations that alter the operation of the device. For example, the engagement rules 226 can indicate to alter the manner in which audio is sensed (e.g., perform audio steering), indicate to alter the manner in which images are sensed (e.g., changing the aperture setting of the camera), indicate to display instructions to the user (e.g., move to a quieter location or provide input via a touchscreen), indicate to change a user interface (e.g., display a text entry box and keyboard rather than a voice input prompt, increase button sizes on a touchscreen, increase or decrease audio output, increase or decrease screen brightness), and so forth.

The device adaptation control 224 is provided to an application or program that the user is engaged with (e.g., a currently active application or program), such as an application 114 or a program of the operating system 112 of FIG. 1. The application or program performs the alteration indicated in the device adaptation control 224. The application or program can continue the adaptation for as long as desired (e.g., until the user is disengaged from the device). The application or program can also invoke additional modules or components to perform various alterations, such as invoking a control module for the microphone 106 of FIG. 1 to perform audio steering. Additionally or alternatively, the device adaptation module 210 can provide to the device adaptation control 224 to such additional modules or components.

Figure 4:
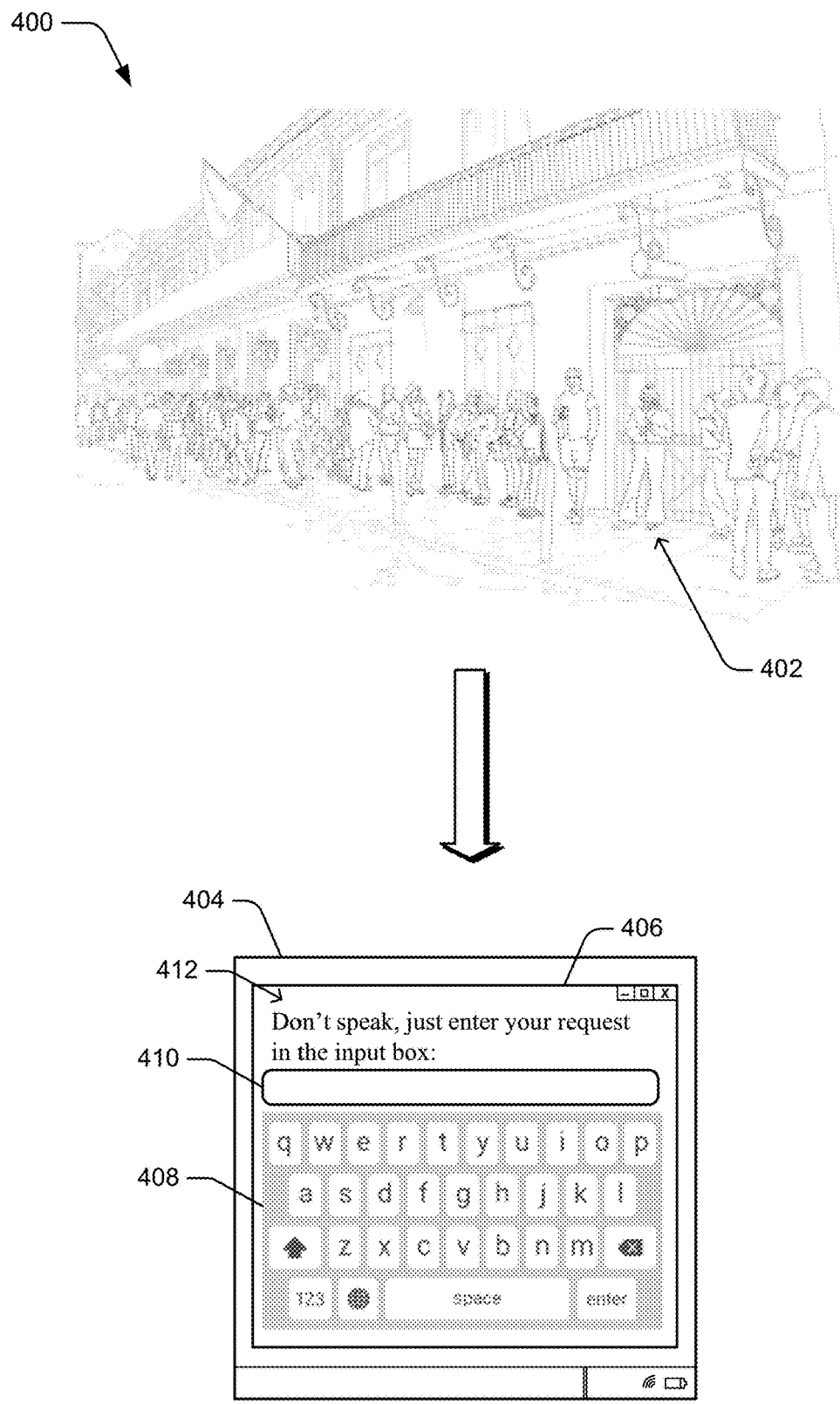
FIG. 4 illustrates an example of the operation of the emotional state based adaptation system.

FIG. 4 illustrates an example 400 of the operation of the emotional state based adaptation system 120. In the example 400 a user 402 is in a noisy environment and is attempting to input an audio command to her computing device. The noisy environment makes voice capture inaccurate so the user 402 gets more and more angry as she repeatedly tries to input the audio command. E.g., the user indicates to the device, after each failed attempt to detect the audio command, that the detection has failed, or from the repeated taps, voice command re-entry, and high repeated pressure taps, and perhaps some captured profanity. The emotional state based adaptation system 120 detects this situation and an engagement rule indicates that if the user is angry while attempting to input an audio command in a noisy environment, prompt the user to enter the request using the device keyboard. The device adaptation module 410 outputs a device adaptation control 224 indicating to alter the operation of the device so that the user is prompted to provide text input. Accordingly, a display 404 of the device displays a user interface 406 with a keyboard 408, a text input box 410, and a prompt 412 indicating for the user to input the request via the keyboard 408 rather than via voice.

Additionally or alternatively, the engagement rule could indicate various other alterations to the operation of the device. For example, the engagement rule could indicate that if the user is angry while attempting to input an audio command in a noisy environment and the device has failed to accurately detect the audio command less than a threshold number of times (e.g., 3), perform audio steering to better sense the voice of the user rather than the noise in the environment. A further engagement rule could indicate that if the user is angry while attempting to input an audio command in a noisy environment and the device has failed to accurately detect the audio command at least a threshold number of times (e.g., 3), prompt the user to enter the request using the device keyboard.

Returning to FIG. 2, by way of further example an engagement rule could indicate that if the user is angry while attempting to input an audio command in a quiet environment and the device has failed to accurately detect the audio command at least a threshold number of times (e.g., 3), prompt the user to enter the request using the device keyboard. Thus, the emotional state based adaptation system 120 can know that since the environment is quiet audio steering will not improve the device's ability to accurately detect the audio command because noise in the environment is not the cause of the failed detection. Rather, the cause of the failed detection is something else (e.g., the user's accent).

By way of another example, an engagement rule could indicate that if the user is agitated or nervous while attempting to input an audio command, has the device close to (e.g., within 1 inch of) the user's face or mouth, and has a low speech spectrum (e.g., the user began talking quieter), then prompt the user to enter the request using the device keyboard. Thus, the emotional state based adaptation system 120 can know that privacy is a concern to the user so she doesn't want to keep repeating an audio command that the device cannot accurately detect (e.g., due to the low speech spectrum), so prompt the user to enter the request using the device keyboard.

It should be noted that the emotional state based adaptation system 120 continues to learn about the user and what environment data 218 triggers which emotional states in the user over time. This learning is performed, for example, by ongoing training of the machine learning systems in the emotional state based adaptation system 120. By continuing to learn about the user the emotional state based adaptation system 120 adapts to changes in the user over time.

For example, a user may keep his mobile phone for several years or transfer the emotional state based adaptation system 120 from one mobile phone to another when he upgrades phones. The user changes as he grows older, so the environment data 218 that results in a particular emotional state in the user when he is 20 years old can be different than when he is 24 years old. E.g., when the user is 20 years old being in an environment of greater than 120 decibels may make the user angry but being in an environment of less than 120 decibels does not make the user angry. However, when the user is 24 years old being in an environment of greater than 110 decibels may make the user angry but being in an environment of less than 110 decibels does not make the user angry.

Furthermore, by continuing to learn about the user the emotional state based adaptation system 120 learns both short-term and long-term effects that the environment data 218 has on the user. For example, the environment data 218 can indicate that the user is eating a large amount of ice cream. The emotional state based adaptation system 120 can learn that eating a large amount of ice cream results in an immediate change in the user emotional state to happy, but after a particular amount of time (e.g., three hours) results in a user emotional state of sluggish. Accordingly, the device adaptation module 210 or other module of the emotional state based adaptation system 120 can provide a reason and emotional state 222 to the device adaptation module 210 indicating the user emotional state is happy due to the ice cream in response to the environment data 218 indicating that the user is eating a large amount of ice cream, and automatically provide a reason and emotional state 222 to the device adaptation module 210 indicating the user emotional state is sluggish due to the ice cream after the particular amount of time (e.g., three hours) has elapsed. In one or more implementations, this reason and emotional state 222 indicating the user emotional state is sluggish due to the ice cream is only sent to (or only acted on by) the device adaptation module 210 in response to user engagement with the device.

By way of another example, the environment data 218 can indicate that the user is attending a yoga class at 8:00 AM. The emotional state based adaptation system 120 can learn that attending a yoga class results in a user emotional state of happy after a particular amount of time (e.g., five hours). Accordingly, the device adaptation module 210 or other module of the emotional state based adaptation system 120 can provide a reason and emotional state 222 to the device adaptation module 210 indicating the user emotional state is happy due to the yoga class after the particular amount of time (e.g., five hours) has elapsed. In one or more implementations, this reason and emotional state 222 indicating the user emotional state is happy due to the yoga class is only sent to (or only acted on by) the device adaptation module 210 in response to user engagement with the device.

Figure 5:
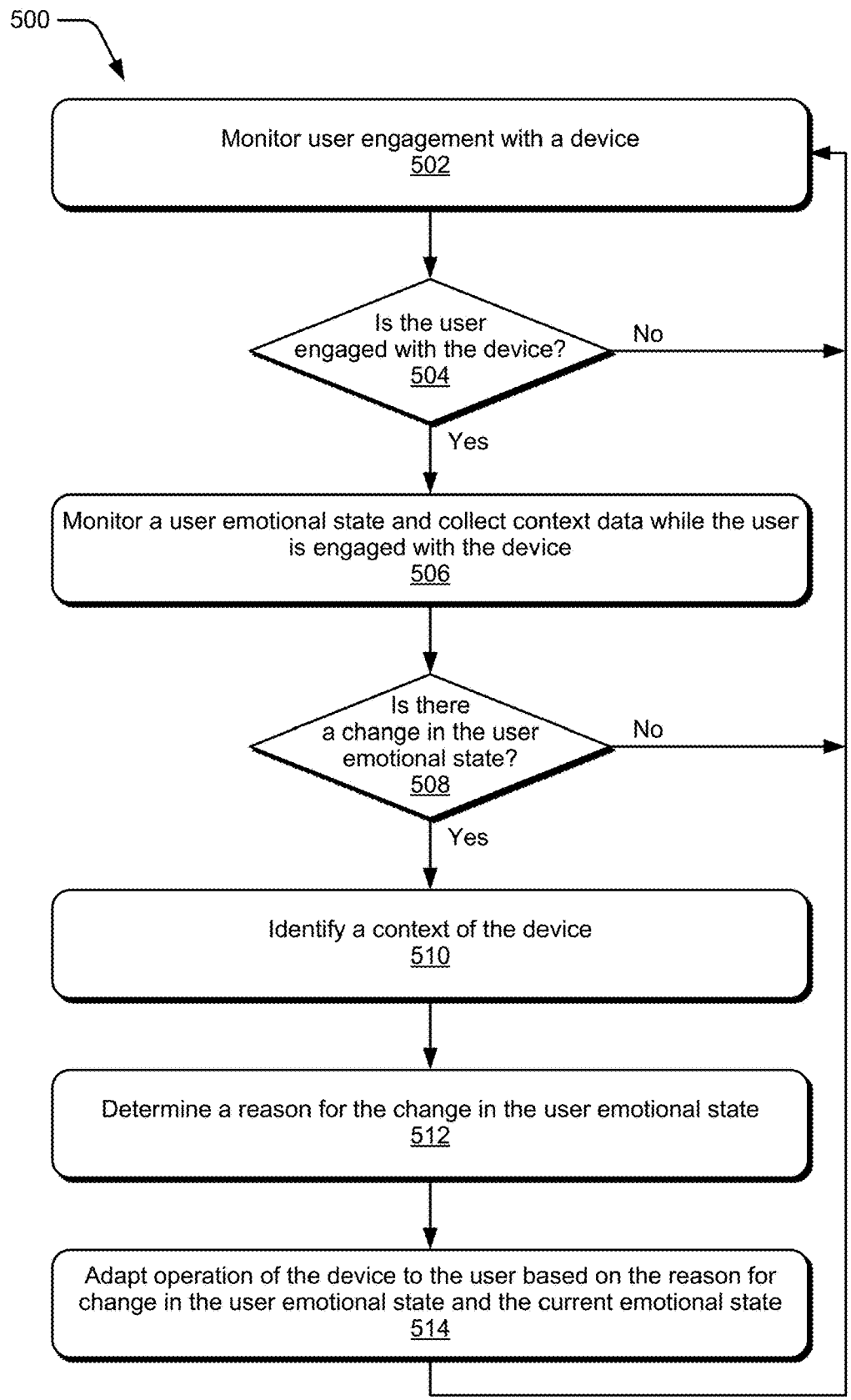
FIG. 5 illustrates an example process for implementing the techniques discussed herein in accordance with one or more embodiments.

FIG. 5 illustrates an example process 500 for implementing the techniques discussed herein in accordance with one or more embodiments. Process 500 is carried out by an emotional state based adaptation system, such as the emotional state based adaptation system 120 of FIG. 1 or FIG. 2, and can be implemented in software, firmware, hardware, or combinations thereof. Process 500 is shown as a set of acts and is not limited to the order shown for performing the operations of the various acts.

In process 500, user engagement with a device is monitored (act 502). This user engagement refers to any user input to or interaction with the device.

A check is made as to whether the user is engaged with the device (act 504). In response to the user being disengaged from (not engaged with) the device, the process returns to act 502 to continue monitoring user engagement with the device.

In response to the user being engaged with the device, an emotional state of the user is monitored and context data for the device is collected while the user is engaged with the device (act 506). This monitoring of the user emotional state can be performed, for example, by a machine learning system classifying the emotional state of the user. The context data includes one or both environment data and sensory data as discussed above.

A check is made as to whether there is a change in the user emotional state (act 508). This change is, for example, a change from a first emotional state to a second emotional state. In response to there being no change in the user emotional state, the process returns to act 502 to continue monitoring user engagement with the device as well as user emotional state and collect context data while the user is engaged with the device.

In response to there being a change in the user emotional state based on prior history of the user, a context of the device is identified (act 510). The context of the device is the context data collected in act 506.

A reason for the change in the user emotional state based on prior history is determined (act 512). This determination is based on the context of the device as well as the current user emotional state. This determination of the reason for the change in the user emotional state can be made, for example, by a machine learning system.

Operation of the device is adapted to the user based on the reason for the change in the emotional state as well as the current emotional state (act 514). This adaptation of the device is an alteration of the operation of the device with a goal, for example, of increasing the likelihood of the user being in a good emotional state (e.g., happy, relaxed) and reducing the likelihood of the user being in a bad emotional state (e.g., sad, angry).

Process 500 then returns to act 502 to continue monitoring user engagement with the device.

Process 500 is an iterative process running continuously on the device in the background while the user is engaged with the device, capturing context data and response data and altering future device engagement with the user to provide emotional friendly engagement. While the user is disengaged from the device the process 500 can monitor user engagement with the device so as to determine whether the user becomes engaged with the device.

Figure 6:
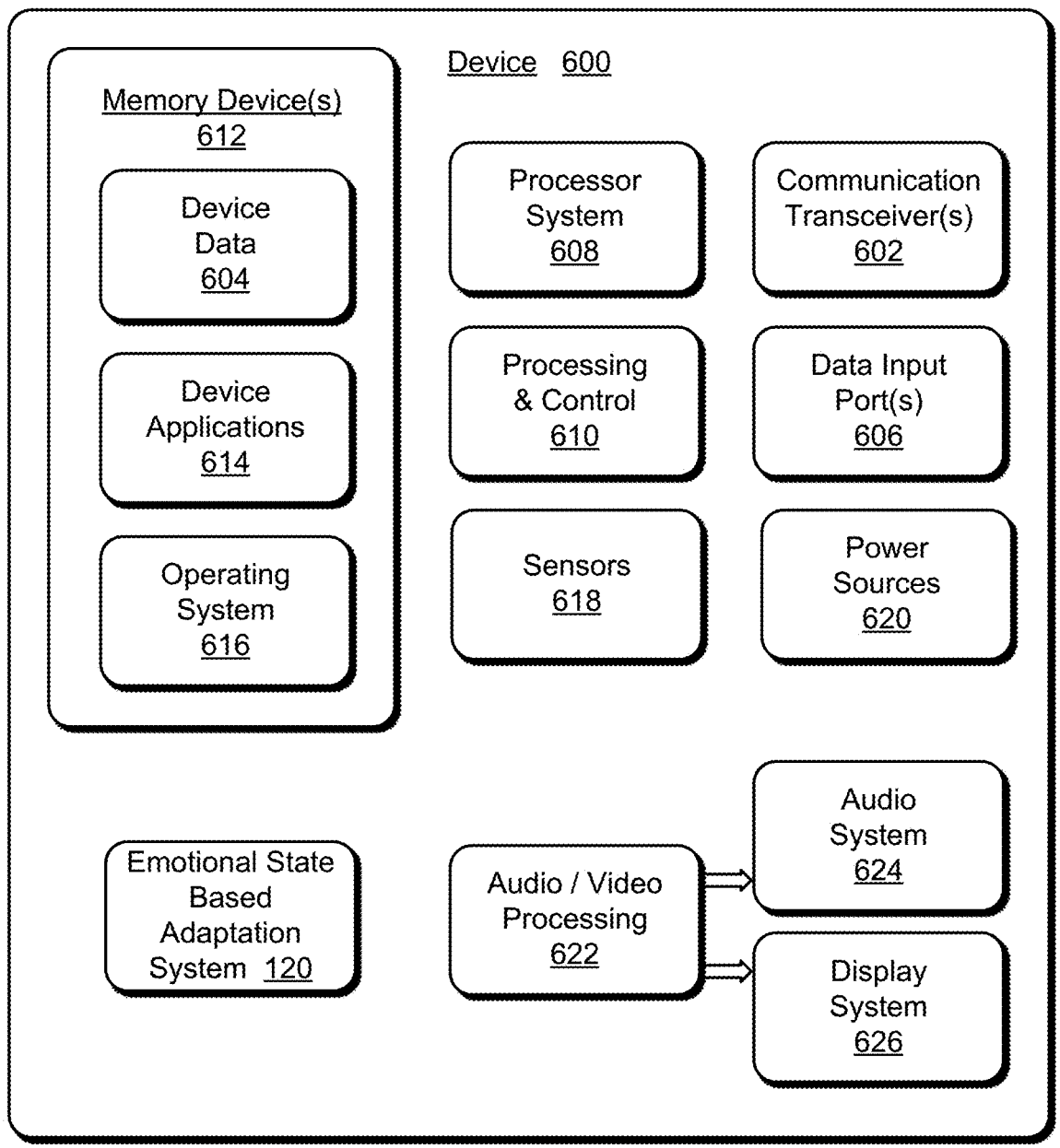
FIG. 6 illustrates various components of an example electronic device that can implement embodiments of the techniques discussed herein.

FIG. 6 illustrates various components of an example electronic device 600 in which embodiments of adapting a device to a user based on user emotional state can be implemented. The electronic device 600 can be implemented as any of the devices described with reference to the previous FIGS., such as any type of client device, mobile phone, tablet, computing, communication, entertainment, gaming, media playback, and/or other type of electronic device. In one or more embodiments the electronic device 600 includes an emotional state based adaptation system 120, described above.

The device 600 includes communication transceivers 602 that enable wired and/or wireless communication of device data 604 with other devices. The device data 604 can include any type of audio, video, and/or image data. Example transceivers include wireless personal area network (WPAN) radios compliant with various IEEE 802.15 (Bluetooth™) standards, wireless local area network (WLAN) radios compliant with any of the various IEEE 802.11 (WiFi™) standards, wireless wide area network (WWAN) radios for cellular phone communication, wireless metropolitan area network (WMAN) radios compliant with various IEEE 802.15 (WiMAX™) standards, and wired local area network (LAN) Ethernet transceivers for network data communication.

The device 600 may also include one or more data input ports 606 via which any type of data, media content, and/or inputs can be received, such as user-selectable inputs to the device, messages, music, television content, recorded content, and any other type of audio, video, and/or image data received from any content and/or data source. The data input ports may include USB ports, coaxial cable ports, and other serial or parallel connectors (including internal connectors) for flash memory, DVDs, CDs, and the like. These data input ports may be used to couple the device to any type of components, peripherals, or accessories such as microphones and/or cameras.

The device 600 includes a processing system 608 of one or more processors (e.g., any of microprocessors, controllers, and the like) and/or a processor and memory system implemented as a system-on-chip (SoC) that processes computer-executable instructions. The processor system 608 may be implemented at least partially in hardware, which can include components of an integrated circuit or on-chip system, an application-specific integrated circuit (ASIC), a field-programmable gate array (FPGA), a complex programmable logic device (CPLD), and other implementations in silicon and/or other hardware.

Alternately or in addition, the device can be implemented with any one or combination of software, hardware, firmware, or fixed logic circuitry that is implemented in connection with processing and control circuits, which are generally identified at 610. The device 600 may further include any type of a system bus or other data and command transfer system that couples the various components within the device. A system bus can include any one or combination of different bus structures and architectures, as well as control and data lines.

The device 600 also includes computer-readable storage memory devices 612 that enable data storage, such as data storage devices that can be accessed by a computing device, and that provide persistent storage of data and executable instructions (e.g., software applications, programs, functions, and the like). Examples of the computer-readable storage memory devices 612 include volatile memory and non-volatile memory, fixed and removable media devices, and any suitable memory device or electronic data storage that maintains data for computing device access. The computer-readable storage memory can include various implementations of random access memory (RAM), read-only memory (ROM), flash memory, and other types of storage media in various memory device configurations. The device 600 may also include a mass storage media device.

The computer-readable storage memory device 612 provides data storage mechanisms to store the device data 604, other types of information and/or data, and various device applications 614 (e.g., software applications). For example, an operating system 616 can be maintained as software instructions with a memory device and executed by the processing system 608. Additionally, although illustrated separate from the computer-readable storage memory device 612, the communication system 106 can be maintained as one of device applications 614. The device applications may also include a device manager, such as any form of a control application, software application, signal-processing and control module, code that is native to a particular device, a hardware abstraction layer for a particular device, and so on.

The device 600 can also include one or more device sensors 618, such as any one or more of an ambient light sensor, a proximity sensor, a touch sensor, an infrared (IR) sensor, accelerometer, gyroscope, thermal sensor, audio sensor (e.g., microphone), and the like. The device 600 can also include one or more power sources 620, such as when the device is implemented as a mobile device. The power sources may include a charging and/or power system, and can be implemented as a flexible strip battery, a rechargeable battery, a charged super-capacitor, and/or any other type of active or passive power source.

The device 600 additionally includes an audio and/or video processing system 622 that generates audio data for an audio system 624 and/or generates display data for a display system 626. In accordance with some embodiments, the audio/video processing system 622 is configured to receive call audio data from the communication system 106 and communicate the call audio data to the audio system 624 for playback at the device 600. The audio system and/or the display system may include any devices that process, display, and/or otherwise render audio, video, display, and/or image data. Display data and audio signals can be communicated to an audio component and/or to a display component via an RF (radio frequency) link, S-video link, HDMI (high-definition multimedia interface), composite video link, component video link, DVI (digital video interface), analog audio connection, or other similar communication link. In implementations, the audio system and/or the display system are integrated components of the example device. Alternatively, the audio system and/or the display system are external, peripheral components to the example device.

Although embodiments of techniques for adapting a device to a user based on user emotional state have been described in language specific to features or methods, the subject of the appended claims is not necessarily limited to the specific features or methods described. Rather, the specific features and methods are disclosed as example implementations of techniques for implementing adapting a device to a user based on user emotional state. Further, various different embodiments are described, and it is to be appreciated that each described embodiment can be implemented independently or in connection with one or more other described embodiments. Additional aspects of the techniques, features, and/or methods discussed herein relate to one or more of the following:

A method comprising: monitoring a user emotional state while a user is engaged with a computing device; detecting that the user emotional state has changed from a first emotional state to a second emotional state; identifying a context of the computing device; determining, based on the context of the computing device, a reason for the change from the first emotional state to the second emotional state; and adapting the computing device to the user by altering operation of the computing device based on the second emotional state and the reason for the change from the first emotional state to the second emotional state.

Alternatively or in addition to the above described method, any one or combination of the following. The context comprising the context of the computing device at the time the user emotional state changed from the first emotional state to the second emotional state. The context comprising environment data describing an environment in which the computing device is present and sensory data associated with the user. The method further comprising ceasing monitoring the user emotional state and ceasing identifying the context of the computing device in response to user disengagement from the computing device. The method further comprising determining that the user is engaged with the computing device in response to receiving a user input. The altering the operation of the computing device comprising altering the operation of the computing device to return the user to the first emotional state. The detecting that the user emotional state has changed from the first emotional state to the second emotional state comprising using a machine learning system to determine the first emotional state to the second emotional state. The determining the reason for the change from the first emotional state to the second emotional state comprising using a machine learning system to determine the reason for the change from the first emotional state to the second emotional state.

A computing device comprising: a processor; and a computer-readable storage medium having stored thereon multiple instructions that implement an emotional state based adaptation system and that, responsive to execution by the processor, cause the processor to perform acts comprising: detecting, while a user is engaged with the computing device, that an emotional state of the user has changed from a first emotional state to a second emotional state; identifying a context of the computing device; determining, based on the context of the computing device, a reason for the change from the first emotional state to the second emotional state; and adapting the computing device to the user by altering operation of the computing device based on the second emotional state and the reason for the change from the first emotional state to the second emotional state.

Alternatively or in addition to the above described computing device, any one or combination of the following. The context comprising the context of the computing device at the time the user emotional state changed from the first emotional state to the second emotional state. The acts further comprising ceasing detecting that an emotional state of the user has changed in response to user disengagement from the computing device. The acts further comprising determining that the user is engaged with the computing device in response to receiving a user input. The altering the operation of the computing device comprising altering the operation of the computing device to return the user to the first emotional state. The detecting that the user emotional state has changed from the first emotional state to the second emotional state comprising using a machine learning system to determine the first emotional state to the second emotional state. The determining the reason for the change from the first emotional state to the second emotional state comprising using a machine learning system to determine the reason for the change from the first emotional state to the second emotional state.

An emotional state based adaptation system comprising: a user emotional state classification module, implemented at least in part in hardware, configured to monitor a user emotional state while a user is engaged with a computing device; an adaptation control module, implemented at least in part in hardware, configured to detect that the user emotional state has changed from a first emotional state to a second emotional state; a context detection module, implemented at least in part in hardware, configured to identify a context of the computing device; a user emotional state reasoning determination module, implemented at least in part in hardware, configured to determine a reason for the change from the first emotional state to the second emotional state based on the context of the computing device; and a device adaptation module, implemented at least in part in hardware, configured to adapt the computing device to the user by altering operation of the computing device based on the second emotional state and the reason for the change from the first emotional state to the second emotional state.

Alternatively or in addition to the above described system, any one or combination of the following. The context comprising the context of the computing device at the time the user emotional state changed from the first emotional state to the second emotional state. The user emotional state classification module ceasing monitoring the user emotional state in response to user disengagement from the computing device, and the context detection module ceasing identifying the context of the computing device in response to user disengagement from the computing device. The altering the operation of the computing device comprising altering the operation of the computing device to return the user to the first emotional state. The user emotional state reasoning determination module includes a machine learning system to determine the reason for the change from the first emotional state to the second emotional state.

What is claimed is:

1. A method comprising:
    monitoring a user emotional state while a user is engaged with a computing device;
    detecting that the user emotional state has changed from a first detected emotional state to a current detected emotional state;
    identifying a context of the computing device based at least in part on environment data that describes an environment in which the computing device is physically present;
    determining, based on the context of the computing device, a reason for the change from the first detected emotional state to the current detected emotional state; and
    adapting the computing device to the user by altering operation of the computing device based on the current detected emotional state and the reason for the change from the first detected emotional state to the current detected emotional state.

2. The method of claim 1, the first detected emotional state comprising a previously detected emotional state and the context comprising the context of the computing device at a time the user emotional state changed from the previously detected emotional state to the current detected emotional state.

3. The method of claim 1, further comprising ceasing monitoring the user emotional state and ceasing identifying the context of the computing device in response to user disengagement from the computing device.

4. The method of claim 1, further comprising determining that the user is engaged with the computing device in response to receiving a user input.

5. The method of claim 1, the altering the operation of the computing device comprising altering the operation of the computing device to return the user to the first detected emotional state.

6. The method of claim 1, the detecting that the user emotional state has changed from the first detected emotional state to the current detected emotional state comprising using a machine learning system to determine the first detected emotional state to the current detected emotional state.

7. The method of claim 1, the determining the reason for the change from the first detected emotional state to the current detected emotional state comprising using a machine learning system to determine the reason for the change from the first detected emotional state to the current detected emotional state.

8. The method of claim 1, the environment data further describing sensory data associated with the user, the sensory data comprising a blood pressure of the user.

9. The method of claim 1, the environment data further describing sensory data associated with the user, the sensory data comprising a loudness of the user.

10. The method of claim 1, the environment data further describing sensory data associated with the user, the sensory data comprising a shift in an acoustical response of user speech.

11. A computing device comprising:
    a processor; and
    a computer-readable storage medium having stored thereon multiple instructions that implement an emotional state based adaptation system and that, responsive to execution by the processor, cause the processor to perform acts comprising:
        detecting, while a user is engaged with the computing device, that an emotional state of the user has changed from a first detected emotional state to a current detected emotional state;
        identifying a context of the computing device based at least in part on environment data that describes an environment in which the computing device is physically present;
        determining, based on the context of the computing device, a reason for the change from the first detected emotional state to the current detected emotional state; and
        adapting the computing device to the user by altering operation of the computing device based on the current detected emotional state and the reason for the change from the first detected emotional state to the current detected emotional state.

12. The computing device of claim 11, the context comprising the context of the computing device at a time the user emotional state changed from the first detected emotional state to the current detected emotional state.

13. The computing device of claim 11, the altering the operation of the computing device comprising altering the operation of the computing device to return the user to the first detected emotional state.

14. The computing device of claim 11, the detecting that the user emotional state has changed from the first detected emotional state to the current detected emotional state comprising using a machine learning system to determine the first detected emotional state to the current detected emotional state.

15. The computing device of claim 11, the determining the reason for the change from the first detected emotional state to the current detected emotional state comprising using a machine learning system to determine the reason for the change from the first detected emotional state to the current detected emotional state.

16. An emotional state based adaptation system comprising:
    a user emotional state classification module, implemented at least in part in hardware, configured to monitor a user emotional state while a user is engaged with a computing device;
    an adaptation control module, implemented at least in part in hardware, configured to detect that the user emotional state has changed from a first detected emotional state to a current detected emotional state;

a context detection module, implemented at least in part in hardware, configured to identify a context of the computing device based at least in part on environment data describing an environment in which the computing device is physically present;

a user emotional state reasoning determination module, implemented at least in part in hardware, configured to determine a reason for the change from the first detected emotional state to the current detected emotional state based on the context of the computing device; and a device adaptation module, implemented at least in part in hardware, configured to adapt the computing device to the user by altering operation of the computing device based on the current detected emotional state and the reason for the change from the first detected emotional state to the current detected emotional state.

17. The emotional state based adaptation system of claim 16, the context comprising the context of the computing device at a time the user emotional state changed from the first detected emotional state to the current detected emotional state.

18. The emotional state based adaptation system of claim 16, the user emotional state classification module ceasing monitoring the user emotional state in response to user disengagement from the computing device, and the context detection module ceasing identifying the context of the computing device in response to user disengagement from the computing device.

19. The emotional state based adaptation system of claim 16, the altering the operation of the computing device comprising altering the operation of the computing device to return the user to the first detected emotional state.

20. The emotional state based adaptation system of claim 16, wherein the user emotional state reasoning determination module includes a machine learning system to determine the reason for the change from the first detected emotional state to the current detected emotional state.

* * * * *